United States Patent
Guo et al.

(10) Patent No.: US 10,112,901 B2
(45) Date of Patent: Oct. 30, 2018

(54) METHOD FOR PREPARING DABIGATRAN ETEXILATE INTERMEDIATE, AND INTERMEDIATE COMPOUND

(71) Applicants: SHANGHAI INSTITUTE OF PHARMACEUTICAL INDUSTRY, Shanghai (CN); CHINA STATE INSTITUTE OF PHARMACEUTICAL INDUSTRY, Shanghai (CN); Chia Tai Tianqing Pharmaceutical Group Co., Ltd., Lianyungang (CN)

(72) Inventors: Yajun Guo, Shanghai (CN); Hanbin Shan, Shanghai (CN); Xueyan Zhu, Shanghai (CN); Zhedong Yuan, Shanghai (CN); Xiong Yu, Shanghai (CN); Meng Guo, Lianyungang (CN); Mingtong Hu, Lianyungang (CN); Duzheng Wang, Lianyungang (CN); Yu Huang, Shanghai (CN)

(73) Assignees: SHANGHAI INSTITUTE OF PHARMACEUTICAL INDUSTRY, Jingan District, Shanghai (CN); CHINA STATE INSTITUTE OF PHARMACEUTICAL INDUSTRY, Pudong New Area, Shanghai (CN); CHIA TAI TIANQING PHARMACEUTICAL GROUP CO., LTD., Lianyungang, Jiangsu Province (CN)

( * ) Notice: Subject to any disclaimer, the term of this patent is extended or adjusted under 35 U.S.C. 154(b) by 0 days.

(21) Appl. No.: 15/323,709

(22) PCT Filed: Jul. 3, 2014

(86) PCT No.: PCT/CN2014/081539
§ 371 (c)(1),
(2) Date: Jan. 3, 2017

(87) PCT Pub. No.: WO2016/000230
PCT Pub. Date: Jan. 7, 2016

(65) Prior Publication Data
US 2017/0190666 A1 Jul. 6, 2017

(51) Int. Cl.
*C07D 213/75* (2006.01)
(52) U.S. Cl.
CPC ................. *C07D 213/75* (2013.01)
(58) Field of Classification Search
CPC .................................................... C07D 213/75
See application file for complete search history.

(56) References Cited

U.S. PATENT DOCUMENTS

| 9,006,448 B2 * | 4/2015 | Reddy ................. C07D 233/56 546/273.4 |
| 9,273,030 B2 * | 3/2016 | Thirumalai Rajan ........ C07D 213/81 |
| 2011/0009382 A1 | 1/2011 | Schunk et al. |
| 2013/0079306 A1 | 3/2013 | Uchida et al. |
| 2013/0158270 A1 | 6/2013 | Gnad et al. |

FOREIGN PATENT DOCUMENTS

| CN | 1861596 A | 11/2006 |
| CN | 102633713 A | 8/2012 |
| CN | 102875529 A | 1/2013 |

(Continued)

OTHER PUBLICATIONS

Yuan, Organic Prep and Procedures international, 46, 376-380, 2014.*

(Continued)

*Primary Examiner* — D Margaret M Seaman
(74) *Attorney, Agent, or Firm* — Tope-McKay & Associates

(57) ABSTRACT

Disclosed are a method for preparing a dabigatran etexilate intermediate, and an intermediate compound. The method for preparing a dabigatran etexilate intermediate 4 comprises: reacting a compound 3 with a $C_1$-$C_3$ alkyl alcohol solution of methylamine in an organic solvent, wherein, X=chlorine, bromine, or iodine. Also disclosed are an intermediate compound 3 and a preparation method thereof. The method for preparing a dabigatran etexilate intermediate of the present invention has the advantages of simple process, easy operation, high yield, and easy purification, thus being suitable for industrial production.

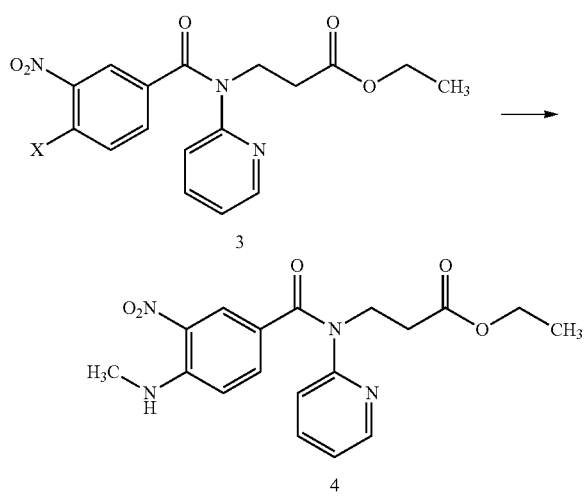

15 Claims, No Drawings

(56) References Cited

FOREIGN PATENT DOCUMENTS

| CN | 102985405 A | | 3/2013 |
|---|---|---|---|
| CN | 103922999 | * | 1/2014 |
| CN | 103922999 A | | 7/2014 |
| CN | 104030977 A | | 9/2014 |
| JP | H07-2839 A | | 1/1995 |
| JP | 2012-92051 A | | 5/2012 |
| JP | 2012-529448 A | | 11/2012 |
| WO | WO2007071743 A1 | | 6/2007 |
| WO | WO2007091950 A1 | | 8/2007 |
| WO | WO2008095928 A1 | | 8/2008 |
| WO | WO2009111997 A1 | | 9/2009 |
| WO | WO2011061080 A1 | | 5/2011 |
| WO | WO 2012/152855 | | 11/2012 |
| WO | WO 2013/111163 | | 8/2013 |
| WO | WO 2013/150545 A2 | | 10/2013 |
| WO | WO2013150545 A2 | | 10/2013 |

OTHER PUBLICATIONS

International Search Report of the International Searching Authority for PCT/CN2014/081539; dated Mar. 25, 2015.

Norbert H. Hauel, et al., "Structure-based design of novel potent nonpeptide thrombin inhibitors," J. Met Chem. 2002, 45, pp. 1757-1766.

Xing Songsong, et al., "Synthesis of Dabigatran Etexilate," Chinese Journal of Pharmaceuticals, Dec. 31, 2010, vol. 5, No. 41, pp. 321-325.

First Office Action issued for corresponding Japanese Patent Application 2017-501166 dated Mar.13, 2018.

Extended European Search Report for European patent application No. 14896440.6; dated Nov. 22, 2017.

Ya-jun Guo Guo, Ya-jun, "A Novel One-pot Synthesis of 3-[(3-Amino-4-methylaminobenzoyl pyridin-2-yl)amino] propionic Acid Ethyl Ester," Organic preparations and procedures international / Org. Prep. Proced. Int., Jul. 10, 2014, vol. 46 Issue: 4, pp. 376-380.

* cited by examiner

METHOD FOR PREPARING DABIGATRAN ETEXILATE INTERMEDIATE, AND INTERMEDIATE COMPOUND

BACKGROUND

Technical Field

The present invention relates to the field of pharmaceutical synthesis, and particularly to a method for preparing a dabigatran etexilate intermediate, and an intermediate compound.

Related Art

Dabigatran etexilate, chemical name ethyl 3-[[[2-[[4-[[[(hexyloxy)carbonyl]amino]iminomethyl]phenyl]amino]toluene]-1-methyl-1H-benzimidazol-5-yl]carbonyl](pyridin-2-yl)amino]propionate, has a chemical structure of Formula 1-1:

is a non-peptide thrombin inhibitor. This drug was first launched in Germany and UK in April, 2008, and then approved by FDA in 2010. The drug can be taken orally, needs no clinical detection, and suffers from few drug interactions.

The synthesis of dabigatran etexilate is particularly described in Patent (or Patent Application) Nos. CN1861596, WO2007/071743, WO2008/095928, WO2009/111997, WO2011/061080, and CN102633713, and also in the literature, J. Med. Chem. 2002, 45, 1757-1766, all of which are incorporated herein by reference in their entirety. In all these literatures, ethyl 3-[(4-methylamino-3-nitrobenzoyl)(pyridin-2-yl)amino]propionate(4) is exclusively used as a key intermediate in the synthesis route. For example, in J. Med. Chem. 2002, 45, 1757-1766, ethyl 3-[(4-methylamino-3-nitrobenzoyl)(pyridin-2-yl)amino]propionate(4) is used as a starting material, which is subjected to reduction, nitrification, condensation and ring closing, ammonolysis of a cyano, and esterification, to

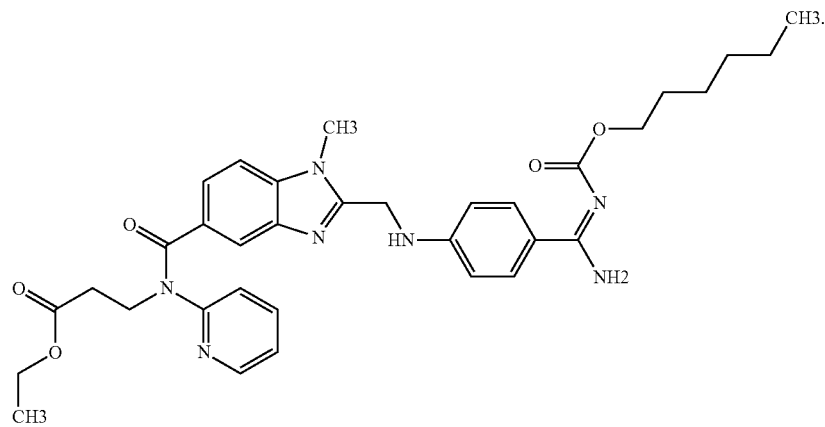

1-1 Dabigatran etexilate

Dabigatran etexilate is a novel oral anti-coagulant developed and launched by Boehringer Ingelheim, Germany, and prepare dabigatran etexilate. The reaction scheme is shown in 1-2.

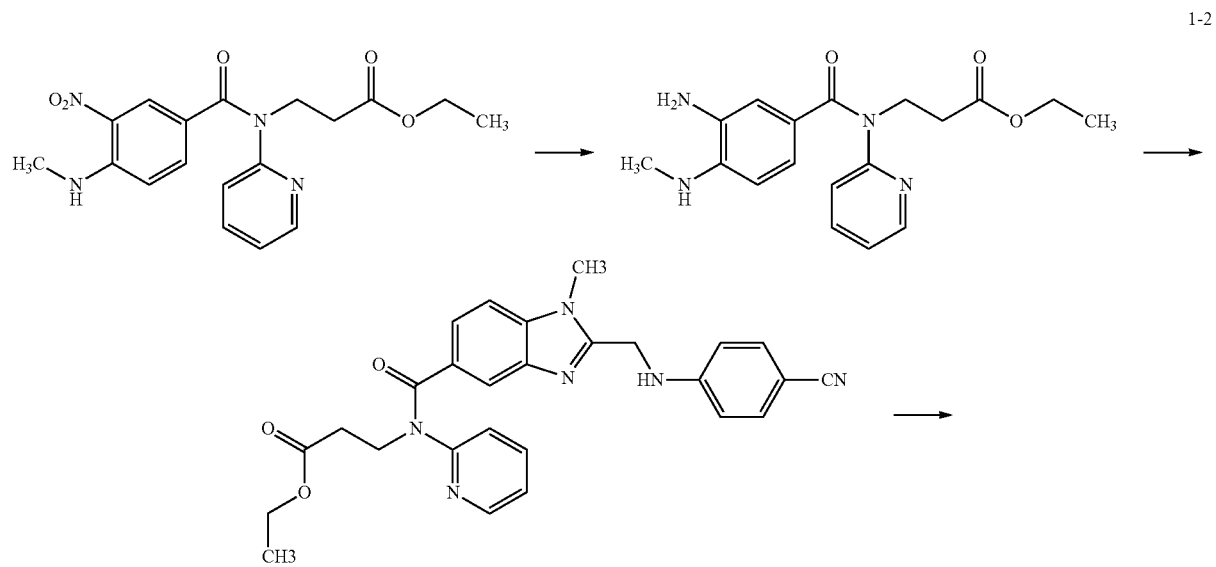

1-2

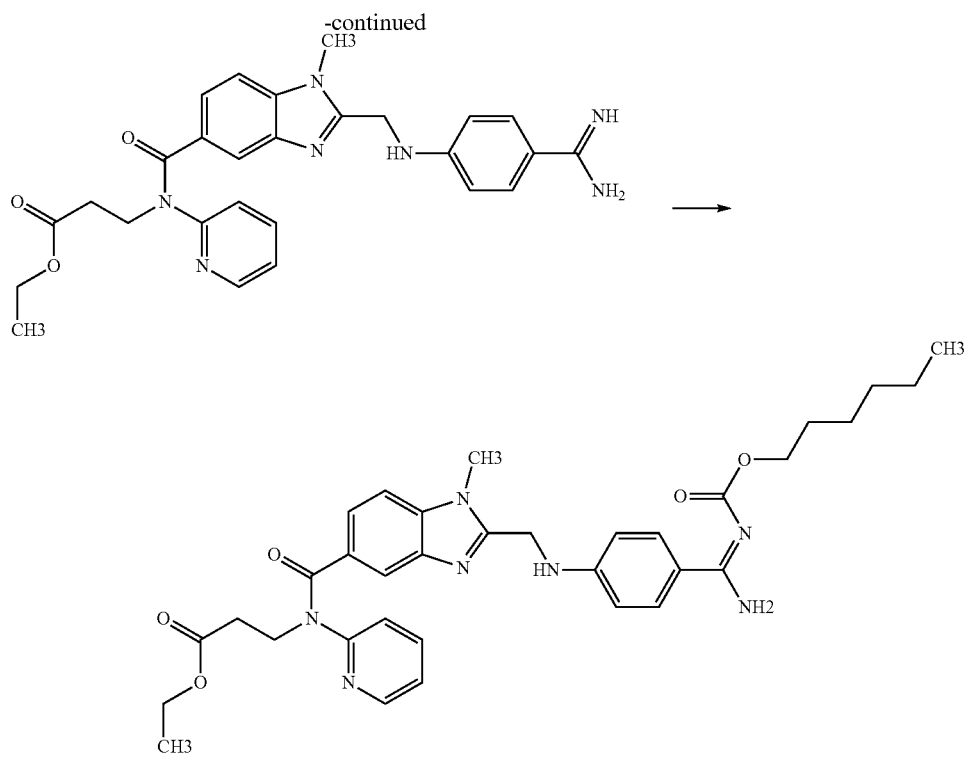

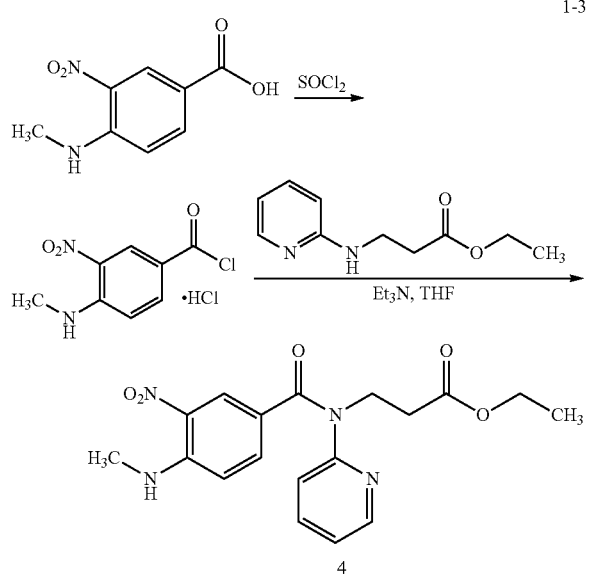

At present, the method for preparing ethyl 3-[(4-methylamino-3-nitrobenzoyl)(pyridin-2-yl)amino]propionate(4) includes: reacting 4-methylamino-3-nitrobenzoic acid with thionyl chloride, to prepare 4-methylamino-3-nitrobenzoyl chloride hydrochloride, which is then acylated with ethyl 3-(pyridin-2-yl-amino)propionate, to prepare ethyl 3-[(4-methylamino-3-nitrobenzoyl)(pyridin-2-yl)amino]propionate(4), as for example described in J. Med. Chem. 2002, 45, 1757-1766. The yield after the two steps is 55%. The reaction scheme is as shown in 1-3:

It can be known from analysis of existing routes for synthesizing ethyl 3-[(4-methylamino-3-nitrobenzoyl)(pyridin-2-yl)amino]propionate(4) that during acylation, 4-methylamino-3-nitrobenzoyl chloride hydrochloride is prone to condensation with itself, after being made free by triethylamine. The side reaction cannot be avoided, resulting in a low yield. In addition, the dripping rate of the tetrahydrofuran solution of 4-methylamino-3-nitrobenzoyl chloride hydrochloride is critical to the acylation. However, this compound is sparingly soluble in tetrahydrofuran, and a large amount of tetrahydrofuran is needed for dissolution, which is disadvantageous in industrial production.

SUMMARY

In view of the technical problem to overcome the deficiency including great difficulty in the current preparation of dabigatran etexilate intermediates, presence of various side reactions, low yield, and difficulty in purification, the present invention provides a method for preparing a dabigatran etexilate intermediate and an intermediate compound. The method for preparing a dabigatran etexilate intermediate of the present invention has the advantages of simple process, easy operation, high yield, and easy purification, thus being suitable for industrial production.

The technical problems are addressed in the present invention by employing the following technical solutions.

The present invention provides a method for preparing a dabigatran etexilate intermediate 4, which includes: reacting a compound 3 with a $C_1$-$C_3$ alkyl alcohol solution of methylamine in an organic solvent, wherein the organic solvent is a protic organic solvent or an aprotic organic solvent; and

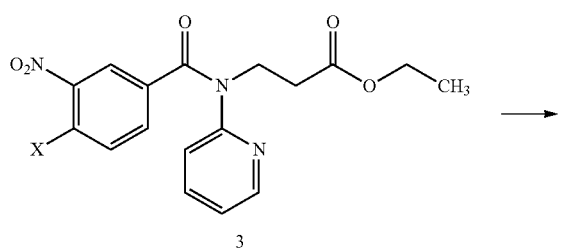

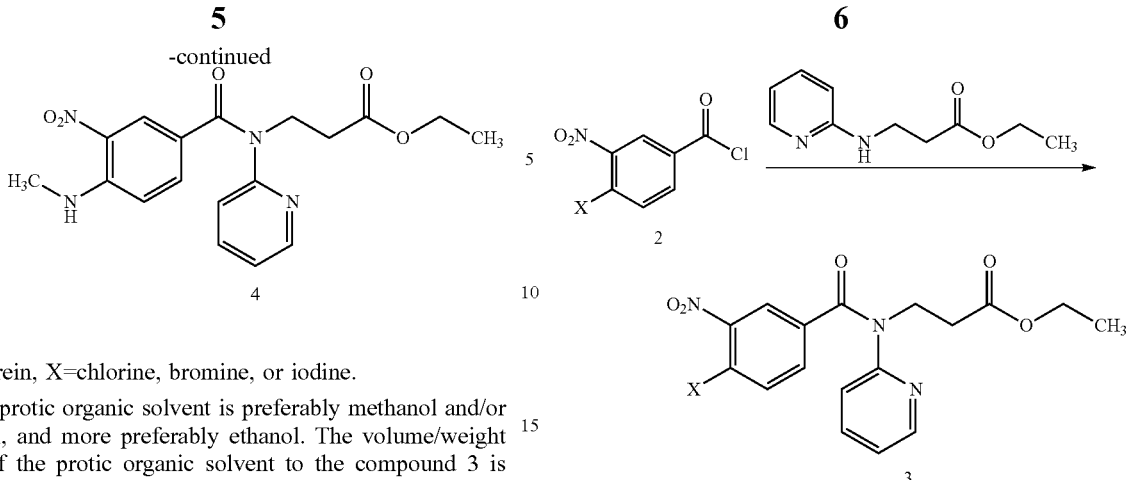

wherein, X=chlorine, bromine, or iodine.

The protic organic solvent is preferably methanol and/or ethanol, and more preferably ethanol. The volume/weight ratio of the protic organic solvent to the compound 3 is preferably 3-5 ml/g. The aprotic organic solvent is preferably an aprotic polar organic solvent, and more preferably one or more of dimethyl sulfoxide, N,N-dimethyl formamide, N,N-dimethyl acetamide, and N-methyl pyrrolidone. The volume/weight ratio of the aprotic organic solvent to the compound 3 is preferably 2.5-5.0 ml/g.

Wherein, X is preferably chlorine.

The $C_1$-$C_3$ alkyl alcohol solution of methylamine is preferably one or more of a methanol solution of methylamine, an ethanol solution of methylamine, and a propanol solution of methylamine, and more preferably an ethanol solution of methylamine.

The concentration of the $C_1$-$C_3$ alkyl alcohol solution of methylamine is 27-32% by weight.

The molar ratio of the compound 3 to methylamine is preferably 1:1.98-1:2.35.

The $C_1$-$C_3$ alkyl alcohol solution of methylamine is preferably added by dripping the $C_1$-$C_3$ alkyl alcohol solution of methylamine into a mixture of the compound 3 and the organic solvent.

When the organic solvent is a protic organic solvent, the reaction temperature is preferably 30-40° C.; and when the organic solvent is an aprotic organic solvent, the reaction temperature is preferably 60-90° C., and more preferably 70° C.

The reaction process may be monitored by conventional means (for example, TLC or HPLC) known in the art. The disappearance of the compound 3 is generally taken as the reaction endpoint, and the reaction time is preferably 0.5-5 hrs.

After the reaction is completed, post-treatment may be performed to further purify the compound 4. The post-treatment may be a conventional post-treatment in the art, and preferably includes: evaporating the reaction solution to dryness and performing column chromatography, when the organic solvent is a protic organic solvent; and adding ethyl acetate, washing with water, drying, filtering, and evaporating the filtrate to dryness when the organic solvent is an aprotic organic solvent. The volume/weight ratio of ethyl acetate to the compound 3 is preferably 1-5 ml/g, and the drying is preferably performed over anhydrous sodium sulfate.

The compound 3 may be prepared through a method including: acylating a compound 2 with ethyl 3-(pyridin-2-yl-amino)propionate in dichloromethane and/or tetrahydrofuran in the presence of an organic base, where X=chlorine, bromine, or iodine.

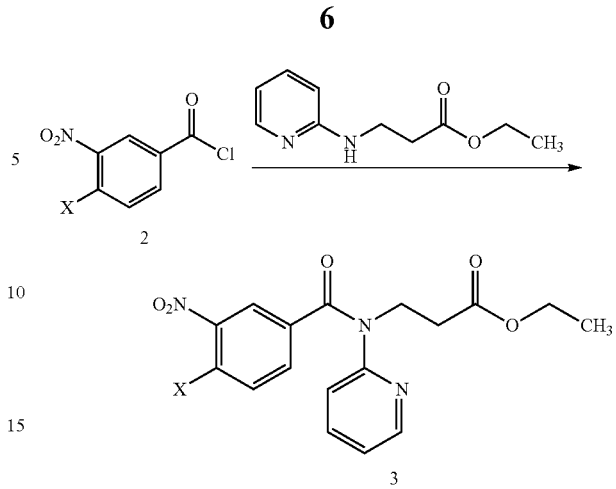

The organic base may be a common organic base that can provide a basic environment in this type of reactions in the art, and is preferably methyl amine and/or N,N-diisopropylethylamine.

The molar ratio of the compound 2 to ethyl 3-(pyridin-2-yl-amino)propionate is preferably 1:1.

The acylation temperature may be conventional acylation temperature in the art, and is preferably 0-30° C.

The volume/weight ratio of dichloromethane and/or tetrahydrofuran to the compound 2 is preferably 4-7 ml/g.

The molar ratio of the organic base to the compound 2 is preferably 1:1-2:1.

The compound 2 is preferably added by adding a mixture of the compound 2 and dichloromethane and/or tetrahydrofuran into a mixture of ethyl 3-(pyridin-2-yl-amino)propionate and the organic base; and more preferably by dripping a mixture of the compound 2 and dichloromethane and/or tetrahydrofuran into a mixture of ethyl 3-(pyridin-2-yl-amino)propionate and the organic base.

The acylation progress may be monitored by conventional means, (for example, TLC or HPLC) known in the art. The disappearance of the ethyl 3-(pyridin-2-yl-amino)propionate is generally taken as the reaction endpoint, and the reaction time is preferably 0.5-2 hrs.

After the acylation is completed, post-treatment may be performed to further purify the compound 3. The post-treatment may be a conventional post-treatment in the art, and preferably includes: washing the reaction solution with water, drying, filtering, evaporating the filtrate to dryness and performing column chromatography.

The present invention further provides a compound 3, which has a structure represented by:

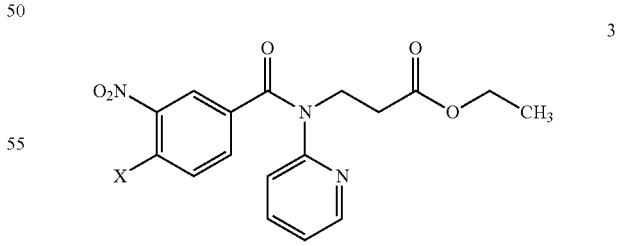

wherein, X=chlorine, bromine, or iodine.

This compound 3 may be used to prepare the dabigatran etexilate intermediate 4.

The present invention further provides a method for preparing the compound 3, which includes: acylating a compound 2 with ethyl 3-(pyridin-2-yl-amino)propionate in dichloromethane and/or tetrahydrofuran in the presence of an organic base, wherein X=chlorine, bromine, or iodine.

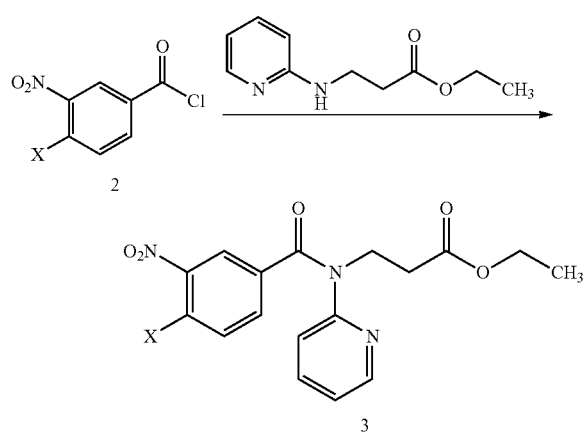

The organic base may be a common organic base that can provide a basic environment in this type of reactions in the art, and is preferably triethylamine and/or N,N-diisopropylethylamine.

The molar ratio of the compound 2 to ethyl 3-(pyridin-2-yl-amino)propionate is preferably 1:1.

The acylation temperature is conventional acylation temperature in the art, and is preferably 0-30° C.

The volume/weight ratio of dichloromethane and/or tetrahydrofuran to the compound 2 is preferably 4-7 ml/g.

The molar ratio of the organic base to the compound 2 is preferably 1:1-2:1.

The compound 2 is preferably added by adding a mixture of the compound 2 and dichloromethane and/or tetrahydrofuran into a mixture of ethyl 3-(pyridin-2-yl-amino)propionate and the organic base; and more preferably by dripping a mixture of the compound 2 and dichloromethane and/or tetrahydrofuran into a mixture of ethyl 3-(pyridin-2-yl-amino)propionate and the organic base.

The acylation progress may be monitored by conventional means (for example, TLC or HPLC) known in the art. The disappearance of the ethyl 3-(pyridin-2-yl-amino)propionate is generally taken as the reaction endpoint, and the reaction time is preferably 0.5-2 hrs.

After the acylation is completed, post-treatment may be performed to further purify the compound 3. The post-treatment may be a conventional post-treatment in the art, and preferably includes: washing the reaction solution with water, drying, filtering, evaporating the filtrate to dryness, and performing column chromatography.

The compound 2 may be prepared through a process including: reacting a compound 1 with thionyl chloride in a mixed solvent of N,N-dimethyl formamide and toluene, wherein X=chlorine, bromine or iodine. For this method, reference may be made to J. Med. Chem. 1989, 32, 409-417, which is incorporated herein by reference in its entirety.

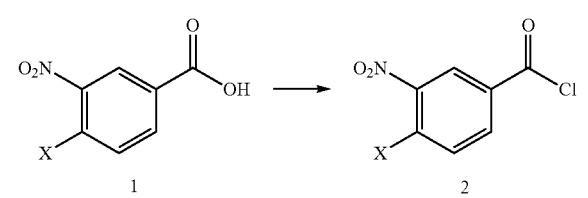

In light of common knowledge in the art, any combination of the preferred conditions as described above may be used to obtain various preferred embodiments of the present invention.

The reagents and raw materials used in the present invention are all commercially available.

The positive and progressive effect of the present invention lies in the method for preparing a dabigatran etexilate intermediate of the present invention having a simple process, ease in operation, a high yield, and ease in purification, which is suitable for industrial production.

DETAILED DESCRIPTION

The present invention is further described by means of examples, but in no way limited to the scope of the examples. For the experimental methods in the following examples where no specific conditions are given, conventional procedures and conditions are used, or procedures and conditions are selected following a product instruction.

Example 1

Synthesis of 3-nitro-4-chlorobenzoyl chloride (Compound 2)

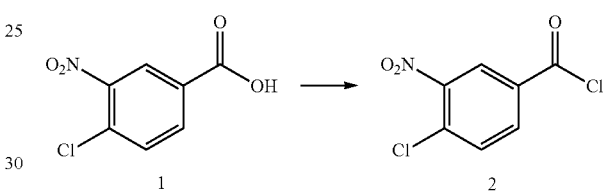

3-nitro-4-chlorobenzoic acid (10.0 g, 49.6 mmol), N,N-dimethyl formamide (0.3 ml, 3.6 mmol) and toluene (50 ml) were added to a reactor, and heated to 70° C. Thionyl chloride (4.3 ml, 59.5 mmol) was added, and heating was resumed to reflux for 30 min. Thionyl chloride and the solvent were distilled away under reduced pressure, to obtain a pale yellow oil (compound 2) which was dissolved in dichloromethane (60 ml) and directly used in the next reaction.

Example 2

Synthesis of ethyl 3-[(3-nitro-4-chlorobenzoyl)(pyridin-2-yl)amino]propionate (Compound 3)

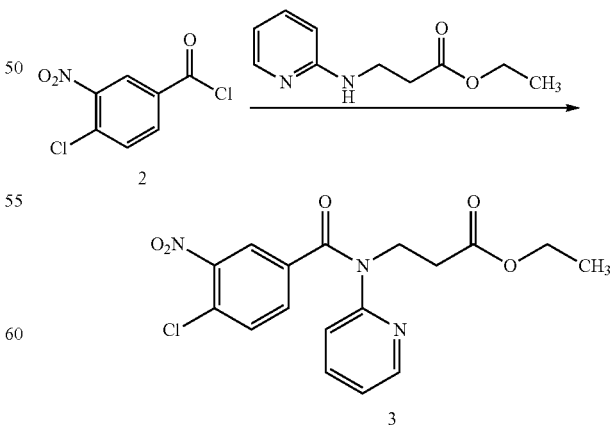

Ethyl 3-(pyridin-2-yl-amino)propionate (9.6 g, 49.6 mmol), triethylamine (13.8 ml, 99.2 mmol), and dichloromethane (20 ml) were added to a reactor, and the dichloromethane solution of the compound 2 obtained in Example 1 was added dropwise, and then stirred at room temperature for 1 hr. The reaction solution was washed with water, dried over anhydrous sodium sulfate, and filtered. The filtrate was evaporated to dryness, and the remaining solid was purified by column chromatography, to obtain the compound 3 (16.3 g, yield 87.0%). mp 63-65° C.; ESI-MS (m/z): 378[M+H]$^+$, 400[M+Na]$^+$; $^1$H-NMR (DMSO-d$_6$, 400 MHz) δ: 1.19 (t, 3H), 2.70 (t, 2H), 3.95 (q, 2H), 4.20 (t, 2H), 7.22 (d, 2H), 7.25 (t, 1H), 7.44 (dd, 1H), 7.66 (d, 1H), 7.75 (m, 1H), 7.92 (d, 1H), 8.35 (dd, 1H). Purity by HPLC: 98.5%.

Example 3

Synthesis of ethyl 3-[(4-methylamino-3-nitrobenzoyl)(pyridin-2-yl)amino]propionate (Compound 4)

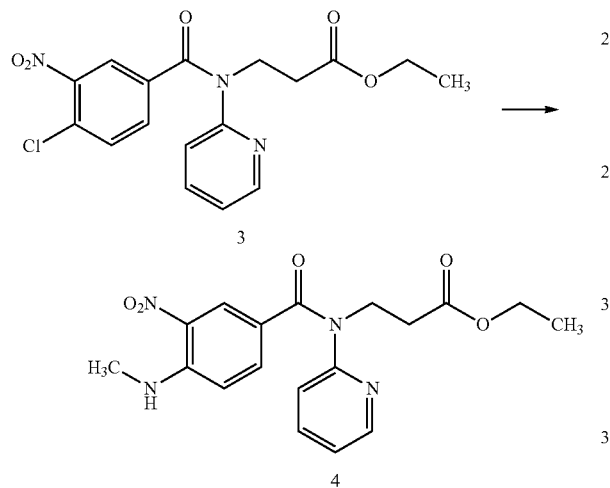

The compound 3 (16.3 g, 47.15 mmol) and ethanol (60 ml) were added to a reactor, and heated to 40° C. A 27.0-32.0% solution (16.3 ml) of methylamine in ethanol was slowly added dropwise, and stirred for 2 hrs. The reaction solution was evaporated to dryness, and the remaining solid was purified by column chromatography, to obtain the compound 4 (13.6 g, yield 84.6%). mp 86-88° C.; $^1$H-NMR (DMSO-d$_6$, 400 MHz) δ: 1.11 (t, 3H), 2.66 (t, 2H), 2.91 (t, 3H), 3.96 (q, 2H), 4.18 (t, 2H), 6.83 (d, 1H), 7.08 (d, 1H), 7.21 (m, 1H), 7.32 (dd, 1H), 7.69 (m, 1H), 7.93 (d, 1H), 8.36 (d, 1H), 8.43 (dd, 1H). Purity by HPLC: 97.9%.

Example 4

Synthesis of 3-nitro-4-chlorobenzoyl chloride (Compound 2)

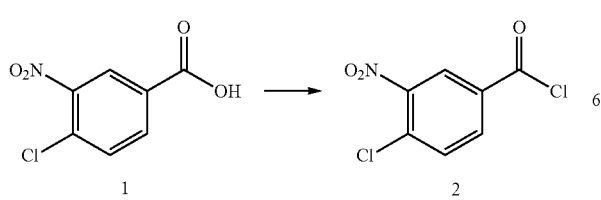

3-nitro-4-chlorobenzoic acid (1.0 g, 4.96 mmol), N,N-dimethyl formamide (0.03 ml, 0.36 mmol), and toluene (8 ml) were added to a reactor, and heated to 70° C. Thionyl chloride (0.43 ml 5.95 mmol) was added, and heating was resumed to reflux for 30 min. Thionyl chloride and the solvent were distilled a way under reduced pressure, to obtain a pale yellow oil (compound 2) which was dissolved in tetrahydrofuran (6 ml) and directly used in the next reaction.

Example 5

Synthesis of ethyl 3-[(3-nitro-4-chlorobenzoyl)(pyridin-2-yl)amino]propionate (Compound 3)

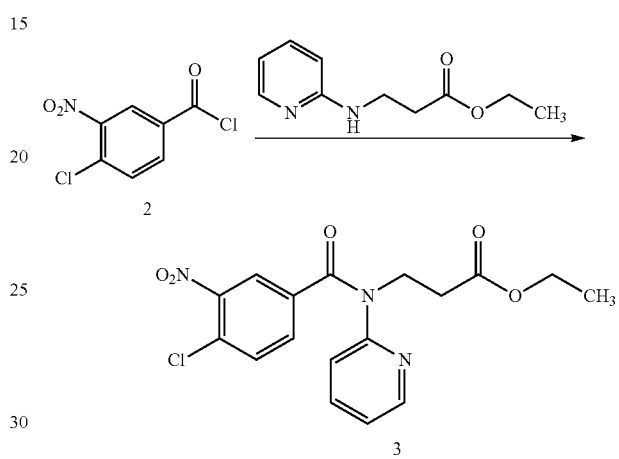

Ethyl 3-(pyridin-2-yl-amino)propionate (0.96 g, 4.96 mmol), triethylamine (1.38 ml, 9.92 mmol), and tetrahydrofuran (4 ml) were added to a reactor, and the tetrahydrofuran solution of the compound 2 obtained in Example 4 was added dropwise, and then stirred at room temperature for 1 hr. The reaction solution as washed with water, dried over anhydrous sodium sulfate, and filtered. The filtrate was evaporated to dryness, and the remaining solid was purified by column chromatography, to obtain the compound 3 (1.59 g, yield 84.9%). mp 63-65° C.; ESI-MS (m/z): 378[M+H]$^+$, 400[M+Na]$^+$; $^1$H-NMR (DMSO-d$_6$, 400 MHz) δ: 1.19 (t, 3H), 2.70 (t, 2H), 3.95 (q, 2H), 4.20 (t, 2H), 7.22 (d, 2H), 7.25 (t, 1H), 7.44 (dd, 1H), 7.66 (d, 1H), 7.75 (m, 1H), 7.92 (d, 1H), 8.35 (dd, 1H). Purity by HPLC: 98.9%.

Example 6

Synthesis of 3-nitro-4-chlorobenzoyl chloride (Compound 2)

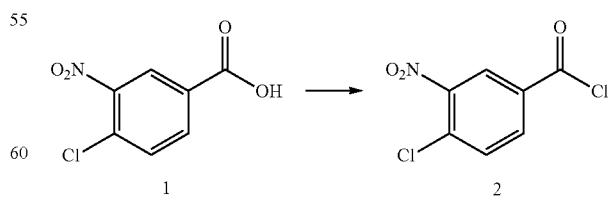

3-nitro-4-chlorobenzoic acid (1.0 g, 4.96 mmol), N,N-dimethyl formamide (0.03 ml, 0.36 mmol) and toluene (8 ml) were added to a reactor, and heated to 70° C. Thionyl chloride (0.43 ml, 5.95 mmol) was added, and heating was resumed to reflux for 30 min. Thionyl chloride and the solvent were distilled away under reduced pressure, to obtain a pale yellow oil (compound 2) which was dissolved in tetrahydrofuran (6 ml) and directly used in the next reaction.

Example 7

Synthesis of ethyl 3-[(3-nitro-4-chlorobenzoyl) (pyridin-2-yl)amino]propionate (Compound 3)

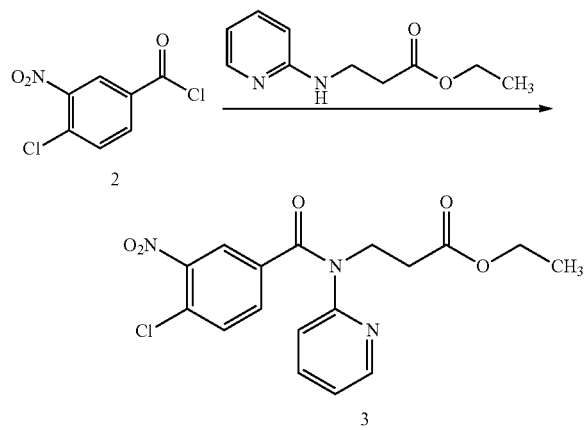

Ethyl 3-(pyridin-2-yl-amino)propionate (0.96 g, 4.96 mmol), N,N-diisopropylethylamine (1.64 ml, 9.92 mmol), and tetrahydrofuran (4 ml) were added to a reactor, and the tetrahydrofuran solution of the compound 2 obtained in Example 6 was added dropwise, and then stirred at room temperature for 1 hr. The reaction solution was washed with water, dried over anhydrous sodium sulfate, and filtered. The filtrate was evaporated to dryness, and the remaining solid was purified by column chromatography, to obtain the compound 3 (1.61 g, yield 85.92%). mp 63-65° C.; ESI-MS (m/z): 378[M+H]$^+$, 400[M+Na]$^+$; $^1$H-NMR (DMSO-d$_6$, 400 MHz) δ: 1.19 (t, 3H), 2.70 (t, 2H), 3.95 (q, 2H), 4.20 (t, 2H), 7.22 (d, 2H), 7.25 (t, 1H), 7.44 (dd, 1H), 7.66 (d, 1H), 7.75 (m, 1H), 7.92 (d, 1H), 8.35 (dd, 1H). Purity by HPLC: 98.7%.

Example 8

The compound 3 (21.2 g, 56.12 mmol) and dimethyl sulfoxide (77.0 ml) were added to a reactor, and heated to 70° C. A 27.0-32.0% solution (21.0 ml) of methylamine in ethanol was slowly added dropwise, and stirred for 30 min. Ethyl acetate (39.0 ml) was added to the reaction solution, washed with water, dried over anhydrous sodium sulfate, and filtered. The filtrate was evaporated to dryness, to obtain the compound 4 (20.6 g, yield 98.56%). mp 86-88° C.; $^1$H-NMR (DMSO-d$_6$, 400 MHz) δ: 1.11 (t, 3H), 2.66 (t, 2H), 2.91 (t, 3H), 3.96 (q, 2H), 4.18 (t, 2H), 6.83 (d, 1H), 7.08 (d, 1H), 7.21 (m, 1H), 7.32 (dd, 1H), 7.69 (m, 1H), 7.93 (d, 1H), 8.36 (d, 1H), 8.43 (dd, 1H). Purity by HPLC: 98.3%.

Example 9

The compound 3 (50 g, 13.24 mmol) and N,N-dimethyl formamide (18.0 ml) were added to a reactor, and heated to 70° C. A 27.0-32.0% solution (5.0 ml) of methylamine in ethanol was slowly added dropwise, and stirred for 30 min. Ethyl acetate (10.0 ml) was added to the reaction solution, washed with water, dried over anhydrous sodium sulfate, and filtered. The filtrate was evaporated to dryness, to obtain the compound 4 (4.8 g, yield 97.36%). mp 86-88° C.; $^1$H-NMR (DMSO-d$_6$, 400 MHz) δ: 1.11 (t, 3H), 2.66 (t, 2H), 2.91 (t, 3H), 3.96 (q, 2H), 4.18 (t, 2H), 6.83 (d, 1H), 7.08 (d, 1H), 7.21 (m, 1H), 7.32 (dd, 1H), 7.69 (m, 1H), 7.93 (d, 1H), 8.36 (d, 1H), 8.43 (dd, 1H). Purity by HPLC: 98.9%.

Example 10

The compound 3 (5.0 g, 13.24 mmol) and N,N-dimethyl acetamide (18.0 ml) were added to a reactor, and heated to 70° C. A 27.0-32.0% solution (5.0 ml) of methylamine in ethanol was slowly added dropwise, and stirred for 30 min. Ethyl acetate (10.0 ml) was added to the reaction solution, washed with water, dried over anhydrous sodium sulfate, and filtered. The filtrate was evaporated to dryness, to obtain the compound 4 (4.9 g, yield 99.39%). mp 86-88° C.; $^1$H-NMR (DMSO-d$_6$, 400 MHz) δ: 1.11 (t, 3H), 2.66 (t, 2H), 2.91 (t, 3H), 3.96 (q, 2H), 4.18 (t, 2H), 6.83 (d, 1H), 7.08 (d, 1H), 7.21 (m, 1H), 7.32 (dd, 1H), 7.69 (m, 1H), 7.93 (d, 1H), 8.36 (d, 1H), 8.43 (dd, 1H). Purity by HPLC: 98.0%.

Example 11

The compound 3 (3.5 g, 9.40 mmol) and N-methyl pyrrolidone (12.6 ml) were added to a reactor, and heated to 70° C. A 27.0-32.0% solution (3.5 ml) of methylamine in ethanol was slowly added dropwise, and stirred for 30 min. Ethyl acetate (7.0 ml) was added to the reaction solution, washed with water, dried over anhydrous sodium sulfate, and filtered. The filtrate was evaporated to dryness, to obtain the compound 4 (3.4 g, yield 98.55%). mp 86-88° C.; $^1$H-NMR (DMSO-d$_6$, 400 MHz) δ: 1.110. (t, 3H), 2.66 (t, 2H), 2.91 (t, 3H), 3.96 (q, 2H), 4.18 (t, 2H), 6.83 (d, 1H), 7.08 (d, 1H), 7.21 (m, 1H), 7.32 (dd, 1H), 7.69 (ms 1H), 7.93 (d, 1H), 8.36 (d, 1H), 8.43 (dd, 1H). Purity by HPLC: 98.8%.

Example 12

The compound 3 (5.0 g, 13.24 mmol) and N,N-dimethyl acetamide (18.0 ml) were added to a reactor, and heated to 90° C. A 27.0-32.0% solution (5.0 ml) of methylamine in ethanol was slowly added dropwise, and stirred for 30 min. Ethyl acetate (10.0 ml) was added to the reaction solution, washed with water, dried over anhydrous sodium sulfate, and filtered. The filtrate was evaporated to dryness, to obtain the compound 4 (4.8 g, yield 97.36%). mp 86-88° C. 1H-NMR (DMSO-d$_6$, 400 MHz) δ: 1.11 (t, 3H), 2.66 (t, 2H), 2.91 (t, 3H), 3.96 (q, 2H), 4.18 (t, 2H), 6.83 (d, 1H), 7.08 (d, 1H), 7.21 (m, 1H), 7.32 (dd, 1H), 7.69 (m, 1H), 7.93 (d, 1H), 8.36 (d, 1H), 8.43 (dd, 1H). Purity by HPLC: 98.4%.

Example 13

The compound 3 (3.5 g, 9.40 mmol) and N-methyl pyrrolidone (12.6 ml) were added to a reactor, and heated to 60° C. A 27.0-32.0% solution (3.5 ml) of methylamine in ethanol was slowly added dropwise, and stirred for 30 min. Ethyl acetate (7.0 ml) was added to the reaction solution, washed with water, dried over anhydrous sodium sulfate, and filtered. The filtrate was evaporated to dryness, to obtain the compound 4 (3.4 g, yield 98.55%). mp 86-88° C.; 1H-NMR (DMSO-d$_6$, 400 MHz) δ: 1.11 (t, 3H), 2.66 (t, 2H), 2.91 (t, 3H), 3.96 (q, 2H), 4.18 (t, 2H), 6.83 (d, 1H), 7.08 (d, 1H), 7.21 (m, 1H), 7.32 (dd, 1H), 7.69 (m, 1H), 7.93 (d, 1H), 8.36 (d, 1H), 8.43 (dd, 1H). Purity by HPLC: 98.4%.

Although the present invention is described above with reference to specific embodiments, it should be understood by those skilled in the art that the description is merely illustrative, and many changes or modifications can be made to the embodiments without departing from the principle and spirit of the present invention. Therefore, the protection scope of the present invention is as defined by the appended claims.

What is claimed is:

1. A preparation method of a dabigatran etexilate intermediate 4, comprising: reacting a compound 3 with a $C_1$-$C_3$ alkyl alcohol solution of methylamine in an organic solvent, wherein the organic solvent is a erotic organic solvent or an aprotic organic solvent; and

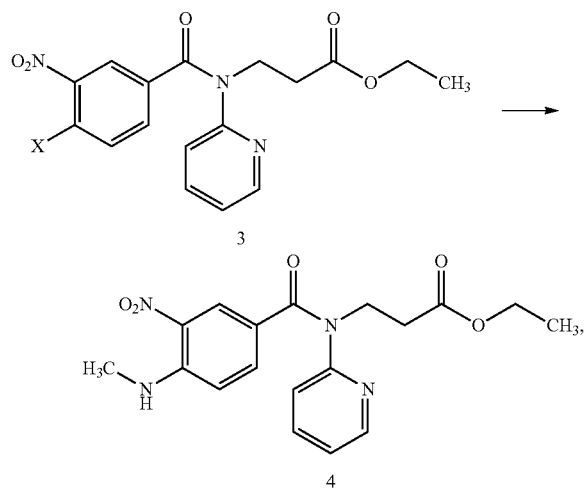

wherein, X=chlorine, bromine, or iodine.

2. The preparation method according to claim 1, wherein the protic organic solvent is methanol and/or ethanol, and the aprotic organic solvent is an aprotic polar organic solvent.

3. The preparation method according to claim 2, wherein the aprotic organic solvent is one or more of dimethyl sulfoxide, N,N-dimethyl formamide, N,N-dimethyl acetamide, and N-methyl pyrrolidone.

4. The preparation method according to claim 1, wherein the $C_1$-$C_3$ alkyl alcohol solution of methylamine is one or more of a methanol solution of methylamine, an ethanol solution of methylamine, and a propanol solution of methylamine; and the concentration of the $C_1$-$C_3$ alkyl alcohol solution of methylamine is 27-32% by weight.

5. The preparation method according to claim 1, wherein the molar ratio of the compound 3 to methylamine is 1:1.98-1:2.35.

6. The preparation method according to claim 1, wherein the $C_1$-$C_3$ alkyl alcohol solution of methylamine is added by dripping the C alkyl alcohol solution of methylamine into a mixture of the compound 3 and the organic solvent.

7. The preparation method according to claim 1, wherein when the organic solvent is a prone organic solvent, the reaction temperature is 30-40° C.; and when the organic solvent is an aprotic organic solvent, the reaction temperature is 60-90° C.

8. The preparation method according to claim 7, wherein when the organic solvent is an aprotic organic solvent, the reaction temperature is 70° C.

9. The preparation method according to claim 1, wherein the compound 3 is prepared through a method comprising: acylating a compound 2 with ethyl 3-(pyridin-2-yl-amino) propionate in dichloromethane and/or tetrahydrofuran in the presence of an organic base; and then the dabigatran etexilate intermediate 4 is prepared following the preparation method according to claim 1,

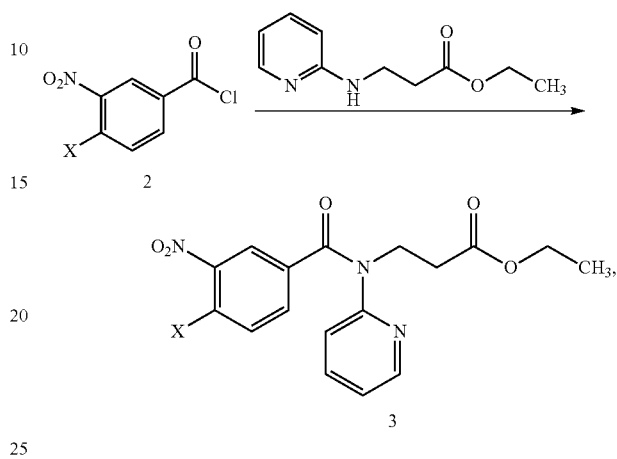

wherein, X=chlorine, bromine, or iodine.

10. The preparation method according to claim 9, wherein the organic base is triethylamine and/or N,N-diisopropyl-ethylamine.

11. The preparation method according to claim 9, wherein the molar ratio of the compound 2 to ethyl 3-(pyridin-2-yl-amino)propionate is 1:1; the molar ratio of the organic base to the compound 2 is 1:1-2:1; and the acylation temperature is 0-30° C.

12. The preparation method according to claim 9, wherein the volume/weight ratio of dichloromethane and/or tetrahydrofuran to the compound 2 is 4-7 ml/g.

13. The preparation method according to claim 9, wherein the compound 2 is added by dripping a mixture of the compound 2 and dichloromethane and/or tetrahydrofuran into a mixture of ethyl 3-(pyridin-2-yl-amino)propionate and the organic base.

14. A compound having a structure represented by

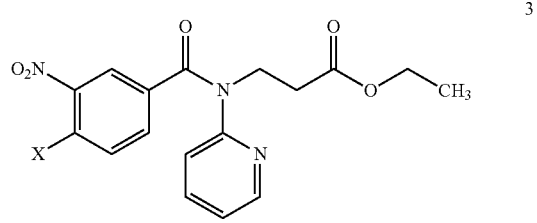

wherein, X=chlorine, bromine, or iodine.

15. A preparation method of the compound 3, represented by:

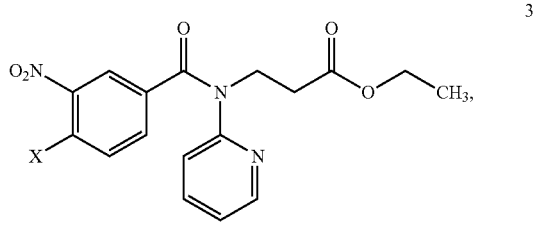

the preparation method comprising: acylating a compound 2 with ethyl 3-(pyridin-2-yl-amino)propionate in dichloromethane and/or tetrahydrofuran in the presence of an organic base,
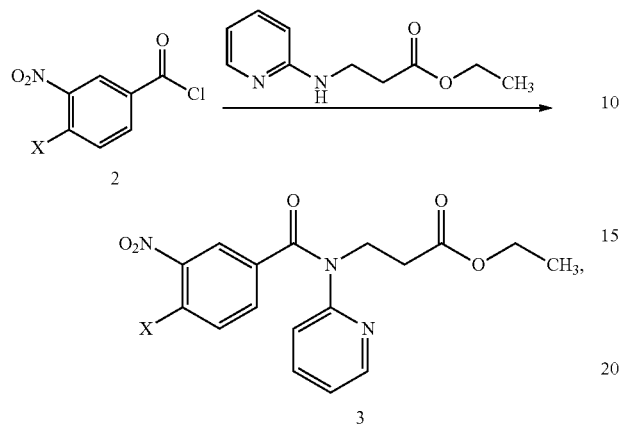
wherein, X=chlorine, bromine, or iodine; and
the reaction conditions in the preparation method are as defined in claim 9.
* * * * *